(12) United States Patent
Dekel

(10) Patent No.: US 11,033,372 B2
(45) Date of Patent: Jun. 15, 2021

(54) PHOTOCURED RESIN BASED ATTACHMENT TO JAW

(71) Applicant: Claronav Inc., North York (CA)

(72) Inventor: Doron Dekel, Toronto (CA)

(73) Assignee: Claronav Inc., North York (CA)

( * ) Notice: Subject to any disclaimer, the term of this patent is extended or adjusted under 35 U.S.C. 154(b) by 338 days.

(21) Appl. No.: 16/200,871

(22) Filed: Nov. 27, 2018

(65) Prior Publication Data

US 2019/0167402 A1 Jun. 6, 2019

Related U.S. Application Data

(60) Provisional application No. 62/595,114, filed on Dec. 6, 2017, provisional application No. 62/618,748, filed on Jan. 18, 2018.

(51) Int. Cl.
| | |
|---|---|
| *A61C 19/04* | (2006.01) |
| *A61B 6/00* | (2006.01) |
| *A61B 6/14* | (2006.01) |
| *A61B 6/03* | (2006.01) |
| *A61B 5/00* | (2006.01) |

(52) U.S. Cl.
CPC .............. *A61C 19/04* (2013.01); *A61B 6/505* (2013.01); *A61B 5/45* (2013.01); *A61B 6/032* (2013.01); *A61B 6/14* (2013.01)

(58) Field of Classification Search
CPC ................................ A61C 19/04; A61B 6/505
See application file for complete search history.

(56) References Cited

U.S. PATENT DOCUMENTS 6,978,167 B2 * 12/2005 Dekel ...................... G06T 7/74
600/426
7,457,443 B2 * 11/2008 Persky ..................... A61B 6/14
128/922

(Continued)

FOREIGN PATENT DOCUMENTS

WO 2016090476 A1 6/2016
WO WO 2016/090476 A1 * 6/2016

OTHER PUBLICATIONS

Written Opinion of the International Searching Authority dated Mar. 7, 2019 in respect of PCT/CA2018/051500.

*Primary Examiner* — Ralph A Lewis
(74) *Attorney, Agent, or Firm* — Bereskin & Parr LLP/S.E.N.C.R.L., s.r.l.

(57) ABSTRACT

A method and system are provided for measuring changes in a pose of a human jaw within a coordinate system of a pose tracking system. The method involves providing a configurable arm; configuring the configurable arm such that at least one rigid target portion of the configurable arm is compliant with operational conditions of the pose tracking system when a selected anchor region of a surface of an anchor portion of the configurable arm is in close proximity to a selected attachment region of the human jaw; positioning the configurable arm such that the anchor region is in close proximity to the attachment region; applying and curing a paste to rigidly couple the anchor region to the attachment region, and operating the pose tracking system to measure changes to the pose of the at least one rigid target portion when the configurable arm is rigidly coupled to the human jaw.

30 Claims, 3 Drawing Sheets

(56) References Cited

U.S. PATENT DOCUMENTS

| | | | | |
|---|---|---|---|---|
| 8,938,282 B2* | 1/2015 | Daon | ..................... | A61B 6/145 |
| | | | | 600/424 |
| 9,844,324 B2* | 12/2017 | Merritt | ............... | A61B 1/00147 |
| 9,943,374 B2* | 4/2018 | Merritt | ................... | A61B 34/20 |
| 2013/0108979 A1* | 5/2013 | Daon | ..................... | A61C 1/082 |
| | | | | 433/29 |
| 2013/0157218 A1 | 6/2013 | Brunner et al. | | |
| 2013/0337400 A1* | 12/2013 | Yi | ............................ | A61B 6/14 |
| | | | | 433/25 |
| 2015/0150641 A1* | 6/2015 | Daon | ..................... | A61B 90/39 |
| | | | | 600/424 |
| 2016/0074127 A1* | 3/2016 | Merritt | ................... | G06T 7/593 |
| | | | | 433/29 |
| 2016/0235483 A1* | 8/2016 | Zeilhofer | ........... | A61B 1/00045 |
| 2018/0279975 A1* | 10/2018 | Dekel | .................... | A61B 6/032 |
| 2019/0328313 A1* | 10/2019 | Hanssen | ............... | A61B 5/1114 |
| 2019/0328466 A1* | 10/2019 | Schwagli | ............... | A61B 34/20 |

* cited by examiner

PHOTOCURED RESIN BASED ATTACHMENT TO JAW

PRIORITY

This application claims the benefit of U.S. Provisional Patent Application No. 62/595,114, filed Dec. 6, 2017 and U.S. Provisional Patent Application No. 62/618,748, filed Jan. 18, 2018, both of which are incorporated herein by reference in their entirety.

FIELD

The described embodiments relate to the field of medicine, in particular, the field of dental navigation systems.

BACKGROUND

Dental navigation systems are increasingly common and commercially available. Many existing dental navigation systems involve the use of a retainer appliance to optically track a subject jaw, that is, a patient's jaw. For example, International Patent Application No. PCT/CA2015/051287 teaches optical tracking of a subject jaw using a retainer appliance that includes a thermoplastic retainer portion and optically tracked targets. The thermoplastic retainer portion is heated up, molded over some teeth of the subject jaw, and then cooled down to harden. After hardening, the retainer appliance provides a rigid and stable coupling between the optically tracked targets placed outside the mouth of the subject jaw, and the subject jaw.

SUMMARY

The various embodiments described herein generally relate to methods (and associated systems configured to implement the methods) for measuring changes in a pose of a human jaw within a coordinate system of a pose tracking system.

An example method involves providing a configurable arm, the configurable arm including an anchor portion and at least one rigid target portion coupled to the anchor portion, a pose of the at least one rigid target portion being trackable by a tracking system when the at least one rigid target portion is compliant with operational conditions of the pose tracking system; configuring the configurable arm such that the at least one rigid target portion is compliant with the operational conditions of the pose tracking system when a selected anchor region of a surface of the anchor portion is in close proximity to a selected attachment region of the human jaw, the selected attachment region of the human jaw including a surface of at least one of the human jaw and a structure rigidly coupled to the human jaw; positioning the configurable arm such that the selected anchor region is in close proximity to the selected attachment region of the human jaw; applying and curing a paste to rigidly couple the anchor region to the attachment region, the paste including a light-curable polymer; and operating the pose tracking system to measure changes to the pose of the at least one rigid target portion when the configurable arm is rigidly coupled to the human jaw, the changes to the pose of the at least one rigid target portion being indicative of the changes in the pose of the human jaw.

In some embodiments, the pose tracking system can be an optical pose tracking system and the at least one rigid target portion can include at least one of a retro-reflective region and a high contrast optical marking.

In some embodiments, the configurable arm can include a metal wire; and configuring the configurable arm can involve bending the metal wire.

In some embodiments, providing a configurable arm can further involve selecting a metal wire biased to resume an initial shape after removal of a transient force of up to about 1 Newton at a distance of up to about 50 millimeters from the anchor region when the configurable arm is rigidly coupled to the human jaw, the initial shape defining an initial spatial relationship between the anchor region and the at least one rigid target portion prior to the transient force.

In some embodiments, providing a configurable arm can further involve providing at least a portion of the anchor portion shaped to resist rolling of the configurable arm about its longitudinal axis within the paste after the paste is cured.

In some embodiments, the at least a portion of the anchor portion shaped to resist rolling can include at least one of a non-circular cross-section and a knurled surface.

In some embodiments, the paste can further include a chemically-curable compound.

In some embodiments, the selected attachment region can include an unetched surface of tooth enamel or dentin, and the paste can be chemically adherable to the selected attachment region at an adhesion strength sufficient for attaching the configurable arm to the selected attachment region and resisting separation of the configurable arm from the selected attachment region when a force of 1 Newton is applied to the configurable arm in any direction at a distance of 50 millimeters from the anchor region.

In some embodiments, the paste can have a viscosity in the range of about 10 Pascal second to about 250 Pascal second.

In some embodiments, the surface of at least one of the human jaw can include a portion of a surface of a tooth of the human jaw.

In some embodiments, the structure rigidly coupled to the human jaw can include at least one of an artificial crown and a dental implant screwed into the human jaw.

In some embodiments, the selected attachment region can include a ceramic surface region, and the method can further involve applying a bonding agent to the ceramic surface region to increase a stickiness of the selected attachment region prior to applying the paste, the bonding agent being light-curable.

In some embodiments, the method can further involve operating a computer and the pose tracking system to determine a registration of the human jaw with a volumetric computed tomography image of the human jaw stored in a computer-readable memory using exposed surfaces of the human jaw outside of the selected attachment region.

In some embodiments, the configurable arm can have a weight of less than about 10 grams.

In some embodiments, the at least one rigid target portion being coupled to the anchor portion can include the at least one rigid target portion being detachably coupled to the anchor portion.

An example system for measuring changes in a pose of a human jaw within a coordinate system of a pose tracking system includes a configurable arm and the pose tracking system. The configurable arm includes an anchor portion and at least one rigid target portion. The anchor portion includes an anchor region of a surface of the anchor portion. The configurable arm has a length sufficient for positioning the anchor region in close proximity to an attachment region of the human jaw while the at least one rigid target portion is compliant with operational conditions of the pose tracking system. The anchor region is rigidly securable by a light-curable paste to the attachment region of the human jaw. The attachment region of the human jaw includes a surface of at least one of the human jaw and a structure rigidly coupled to the human jaw. The at least one rigid target portion is trackable by the pose tracking system. The pose tracking system is configured for measuring changes to the pose of the at least one rigid target portion. The changes in the pose of the at least one rigid target portion is indicative of the changes in the pose of the human jaw.

In some embodiments, the pose tracking system can be an optical pose tracking system and the at least one rigid target portion can include at least one of a retro-reflective region and a high contrast optical marking.

In some embodiments, the configurable arm can include a bendable metal wire.

In some embodiments, the bendable metal wire can include a wire biased to resume an initial shape after removal of a transient force of up to about 1 Newton at a distance of up to about 50 millimeters from the anchor region when the configurable arm is rigidly coupled to the human jaw, the initial shape defining an initial spatial relationship between the anchor region and the at least one rigid target portion prior to the transient force.

In some embodiments, at least a portion of the anchor portion of the configurable arm can be shaped to resist rolling of the configurable arm about its longitudinal axis within the light-curable paste after the paste is cured.

In some embodiments, the at least a portion of the anchor portion shaped to resist rolling can include at least one of a non-circular cross-section and a knurled surface.

In some embodiments, the system can further include the light-curable paste and the light-curable paste can further include a chemically-curable compound.

In some embodiments, the attachment region can include an unetched surface of tooth enamel or dentin, and the light-curable paste is chemically adherable to the attachment region at an adhesion strength sufficient for attaching the configurable arm to the attachment region and resisting separation of the configurable arm from the attachment region when a force of 1 Newton is applied to the configurable arm in any direction at a distance of 50 millimeters from the anchor region.

In some embodiments, the light-curable paste can have a viscosity in the range of about 10 Pascal-second to about 250 Pascal-second.

In some embodiments, the surface of at least one of the human jaw can include a portion of a surface of a tooth of the human jaw.

In some embodiments, the structure rigidly coupled to the human jaw can include at least one of an artificial crown and a dental implant screwed into the human jaw.

In some embodiments, the attachment region can include a ceramic surface region, and the system further comprises a light-curable bonding agent for application to the ceramic surface region to increase a stickiness of the attachment region.

In some embodiments, the system can further include a computer configured for determining a registration of the human jaw with a volumetric computed tomography image of the human jaw stored in a computer-readable memory using exposed surfaces of the human jaw outside of the selected attachment region.

In some embodiments, the configurable arm can have a weight of less than about 10 grams.

In some embodiments, the at least one rigid target portion can be detachably couplable to the anchor portion.

BRIEF DESCRIPTION OF THE DRAWINGS

Several embodiments will now be described in detail with reference to the drawings, in which.

Figure 1:
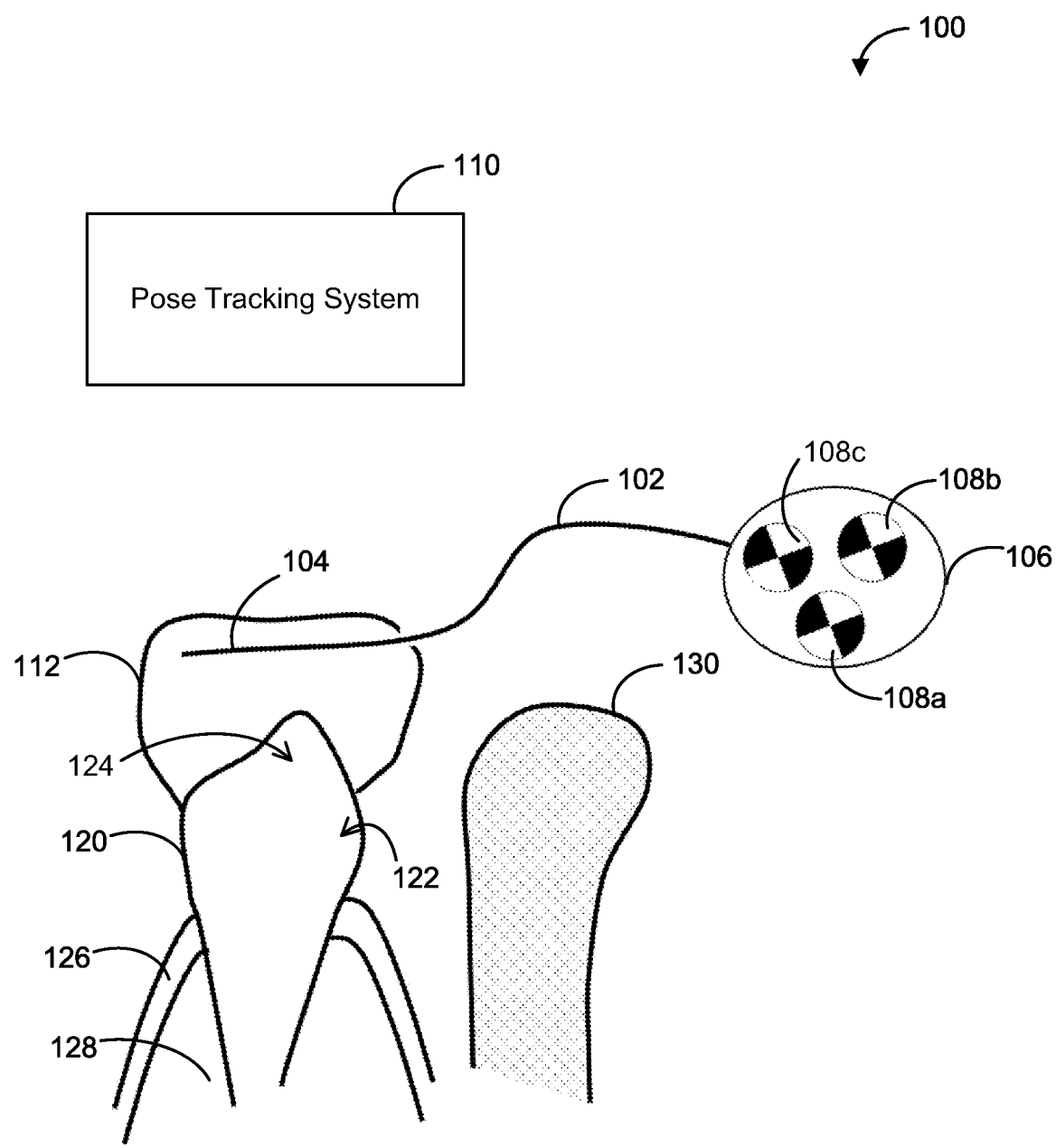
FIG. 1 is an example illustration of a system for measuring changes in a pose of a human jaw within a coordinate system of a pose tracking system.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

In embodiments, aspects of methods described herein, such as method 400 described with reference to FIG. 4 below, may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication component. For example and without limitation, the programmable computer (referred to below as data processor) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication component may be a network communication interface. In embodiments in which elements are combined, the communication component may be a software communication interface, such as those for inter-process communication (IPC). In still other embodiments, there may be a combination of communication components implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

The steps of heating, molding and cooling a retainer appliance in order to track a subject jaw can delay the dental navigation process. In some cases, the steps can require at least five (5) minutes. Furthermore, retainer appliances can, on occasion, fail to produce the desired result due to a variety of reasons. For example, the subject jaw may have an insufficient number of teeth to which the retainer can be molded to, the subject jaw may lack retaining teeth undercuts, or gaps can occur between the retainer appliance and the teeth that the retainer appliance has been molded to.

It is desirable for a method of rigidly attaching trackable markings to a human jaw to be quick and non-invasive. The subject matter of the present application can enable a dental navigation system to measure changes in a pose of a human jaw within a coordinate system of a pose tracking system.

Reference is first made to FIG. 1, which is an example illustration of a system 100 for measuring changes in a pose of a human jaw within a coordinate system of a pose tracking system. The human jaw relates to a jaw bone 128. As shown in FIG. 1, the jaw bone 128 can include a structure rigidly coupled to the jaw bone 128, such as tooth 120, a cross-section of which is shown in FIG. 1: The tooth 120 is embedded in the jaw bone 128 and perpendicular to a ridge 126 of the jaw bone 128. A buccal (i.e., cheek-facing) side 122 of the tooth 120 is proximal to the lip 130.

The tooth 120 can be a natural tooth or an artificial structure of any type that is rigidly coupled to the jaw bone 128. For example, it can be an artificial crown, or a dental implant (not shown) that is screwed into the jaw bone 128. The tooth 120, particularly when it is a natural tooth, can have an unetched surface of tooth enamel or dentin. In some embodiments, the tooth 120 can have a metallic surface or ceramic surface, including a glazed ceramic surface.

As shown in FIG. 1, the system 100 includes a configurable arm 102 and a pose tracking system 110. The configurable arm 102 includes an anchor portion 104 and at least one rigid target portion 106. The at least one rigid target portion 106 is trackable by the pose tracking system 110. Although only one rigid target portion 106 is shown in FIG. 1, in some embodiments, the configurable arm 102 can include more rigid target portions. Similarly, although only one pose tracking system 110 is shown in FIG. 1, the system 100 can include more pose tracking systems.

The anchor portion 104 includes an anchor region of a surface of the anchor portion 104. The anchor region 104 is rigidly securable by a paste 112 to an attachment region 124 of the human jaw 128. For example, as shown in FIG. 1, the anchor portion 104 can be embedded in the paste 112 affixed on attachment region 124 of the human jaw 128. The attachment region 124 can be a portion of an external surface of the human jaw 128, including a portion of an external surface of a structure rigidly coupled to the human jaw 128. For example, as shown in FIG. 1, the attachment region 124 is a portion of an external surface of tooth 120, which is rigidly coupled to the jaw bone 128.

The configurable arm 102 has a length sufficient for positioning the anchor region 104 in close proximity to the attachment region 124 of the tooth 120 while the at least one rigid target portion 106 is compliant with operational conditions of the pose tracking system 110. That is, the configurable arm 102 has a length sufficient for the anchor portion 104 to be positioned in close proximity to the tooth 120 while the at least one rigid target portion 106 is placed outside of the mouth so that the pose tracking system 110 can uninterruptedly detect the at least one rigid target portion 106. That is, so that the at least one rigid target position 106 is within a field of detection of the pose tracking system 110.

The pose tracking system 110 is configured for measuring changes to the pose of the at least one rigid target portion 106. The changes in the pose of the at least one rigid target portion 106 is indicative of the changes in the pose of the human jaw 128. The pose tracking system 110 can track the pose of the at least one rigid target portion 106 at a sufficiently high accuracy and sufficiently low latency for the targeted application of the system. In some embodiments, the pose tracking system 110 can include a detection device for tracking the at least one rigid target portion 106, a processor operatively coupled to the detection device, and a memory operatively coupled to the processor.

In some embodiments, the pose tracking system 110 can be an optical pose tracking system, for example, the MicronTracker™ by ClaroNav™ Inc. When the pose tracking system 110 is an optical pose tracking system, the at least one rigid target portion 106 can include high contrast optical markings 108a, 108b, and 108c (herein collectively referred to as 108) as shown in FIG. 1. Although three high contrast optical markings 108 are shown in FIG. 1, in some embodiments, the at least one rigid target portion 106 can include fewer or more high contrast optical markings 108. In some embodiments, the at least one rigid target portion 106 can include one or more retro-reflective regions and the optical pose tracking system can include a tracking camera and a source of illumination placed near the lenses of the tracking camera such that a contrast between the surface of the retro-reflective region and the surrounding surfaces is created in the camera's image. The one or more retro-reflective regions can have any appropriate shape, including a spherical shape. In other embodiments, a magnetic tracking system may be used and the at least one rigid target portion 106 may contain a magnetic field sensing coil.

In some embodiments, the configurable arm 102 can be a wire formed of any appropriate metal or alloy. For example, the configurable arm 102 can be formed of an annealed metal wire such as Mibro® KingChain® 14-Gauge soft steel galvanized wire. Optionally, the wire can also be embedded in an elastic sleeve.

The configurable arm 102 is adjustable. In some embodiments, the configurable arm 102 can be bendable or pliable, allowing the configurable arm 102 to be bent to a configuration that positions the at least one rigid target portion 106 within the field of detection of the pose tracking system 110 while the anchor portion 104 is rigidly coupled to the human jaw 128. In addition to positioning the at least one rigid target portion 106 within the field of detection of the pose tracking system 110, the configurable arm 102 can also be positioned in a manner that does not create an obstruction to access to the human jaw 128 or that reduces the likelihood that the configurable arm 102 interferes with a dental procedure being performed on the human jaw 128.

While the configurable arm 102 is adjustable, the configurable arm 102 is also sufficiently rigid to maintain its shape or configuration during the dental procedure being performed. That is, the configurable arm 102 can maintain a fixed spatial relationship between at least one rigid target portion 106 and the anchor portion 104. The configurable arm 102 can have an initial shape that defines an initial spatial relationship between the anchor region and the at least one rigid target portion 106. In addition, once adjusted to a desired configuration, the configurable arm 102 is sufficiently rigid to maintain the desired configuration. In some embodiments, such as when the configurable arm 102 includes a 14-Gauge annealed steel wire, the configurable arm 102 can be sufficiently elastic to withstand a transient force of up to about 1 Newton at a distance of up to about 50 millimeters from anchor region 104 to resume its shape after the removal of the transient force.

In some embodiments, the at least one rigid target portion 106 can be detachably couplable to the anchor portion 104. For example, the configurable arm 102 can include a mechanism to fasten the anchor portion 104 and the at least one rigid target portion 106 together. In some embodiments, the mechanism can be a holding screw. When the at least one rigid target portion 106 and the anchor portion 104 are detachable, the anchor portion 104 alone can be first rigidly coupled to the human jaw 128. Once the anchor portion 104 is rigidly coupled to the human jaw 128, the at least one rigid target portion 106 can be fastened to the anchor portion 104.

Coupling a smaller component to the human jaw 128, such as the anchor portion 104 alone, can be easier than coupling a larger component to the human jaw 128, such as the entire configurable arm 102. Furthermore, coupling a smaller component may only require a single application of paste 112 to the tooth 120 whereas coupling a larger component may require multiple applications of paste 112. Furthermore, when the at least one rigid target portion 106 and the anchor portion 104 are detachable, the at least one rigid target portion 106 may be reused.

To prevent undesired rolling of the configurable arm 102 about its longitudinal axis within the paste 112, in some embodiments, at least a portion of the anchor portion 104 of the configurable arm 102 can be shaped to resist rolling of the configurable arm 102 about its longitudinal axis when embedded within the paste 112 after the paste 112 is cured. For example, the anchor portion 104 can have a non-circular cross-section and/or a knurled surface.

Figure 2A:
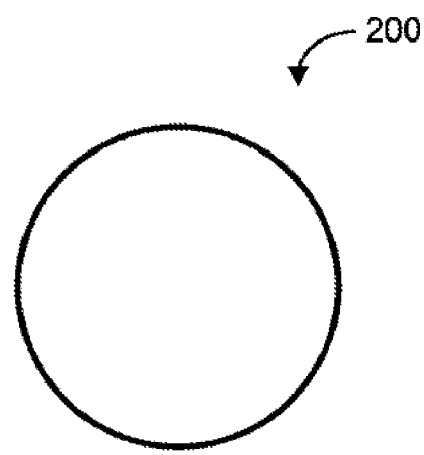
FIG. 2A is an example illustration of a configurable arm having a circular cross-section.
Figure 2B:
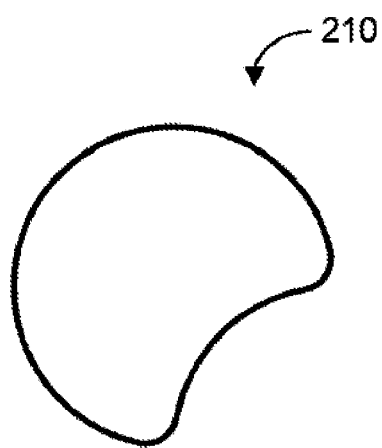
FIG. 2B is an example illustration of a configurable arm having a non-circular cross-section.

FIGS. 2A and 2B illustrate example cross-sections of configurable arms. A configurable arm shown in FIG. 2A has a circular cross-section 200 and a smooth surface. In contrast, configurable arm shown in FIG. 2B has a non-circular cross-section, and more specifically, a cross-section with a concave edge 210. In some embodiments, the non-circular cross-section can include a flat edge instead of, or in addition to, the concave edge 210. In some embodiments, the configurable arm can have a surface that is knurled or roughened to increase its resistance to rolling within the paste 112 after the paste 112 is cured.

The paste 112 for securing the anchor region 104 to the attachment region 124 of the human jaw 128 can be applied to coat the external surface of the attachment region 124. While FIG. 1 shows only a single tooth 120, additional teeth adjacent to tooth 120 may also be coated by the paste 112 to provide a stronger attachment of the configurable arm 102 to the human jaw 128. However, it can be advantageous to cover fewer teeth, which is less invasive. Furthermore, the attachment region 124 is a relatively smaller area than the area covered by a typical retainer appliance. The present subject matter can be safer because the configurable arm 102 is only in contact with the smaller area of the attachment region 124 whereas the typical retainer appliance is adhered to a larger area of the human jaw 128. Furthermore, the present subject matter can also be easier to perform since the smaller area of the attachment region 124 is easier to control.

Figure 3:
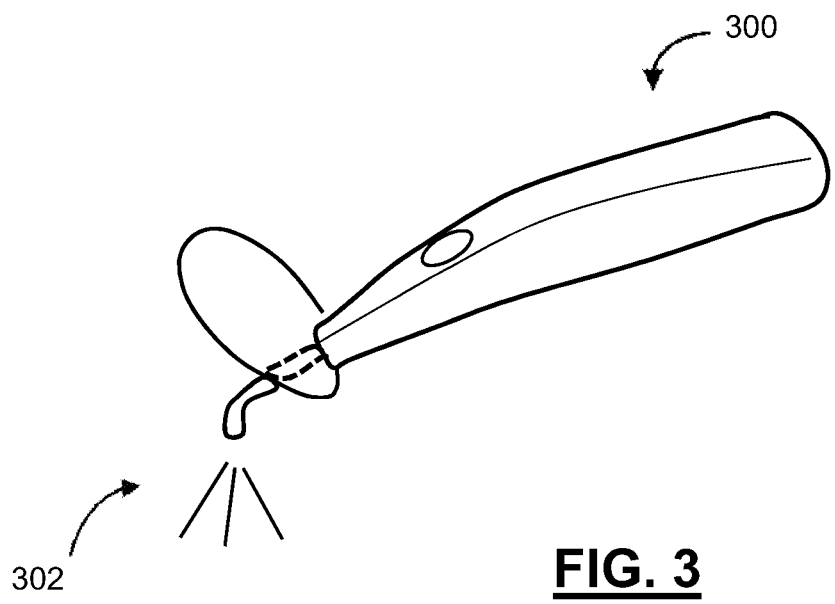
FIG. 3 is an example illustration of a curing light device.

The paste 112 can be a light-curable polymer. In some embodiments, the paste 112 can also be a chemically-curable compound. A curing light device can be used to emit an appropriate activation light onto the paste 112. When subjected to the appropriate activation light, the paste 112 can form a rigid external shell that holds the anchor portion 104 in place or in a desired position while the core of the paste 112 completes curing chemically. FIG. 3 shows an example curing light device 300 that can be used to emit an activation light 302 for curing the paste 112.

In some embodiments, the paste 112 has a low viscosity, for example, a viscosity in the range of about 10 Pascal-second (Pa·s) to about 250 Pascal-second (Pa·s). An example of a light-curable polymer 112 is Grandio® Core Dual Cure, made by VOCO® GmbH.

Optionally, the paste 112 can have a color that is distinguishable from teeth 120, that is, non-white so that the paste 112 is easily identifiable for removal from the tooth 120. At the completion of the dental procedure, the paste 112 can be removed from the tooth 120 by pulling the configurable arm 102 away from the tooth 120.

When the attachment region 124 is an unetched surface of tooth enamel or dentin (i.e., when the tooth 120 is a natural tooth), the paste 112 can be chemically adherable to the attachment region 124 with an adhesion strength sufficient for attaching the configurable arm 102 to the attachment region 124. Furthermore, after curing, the paste 112 can resist separation of the configurable arm 102 from the attachment region 124 when a force of 1 Newton is applied to the configurable arm 102 in any direction at a distance of 50 millimeters from the anchor region. When the above mentioned Grandio® Core Dual Cure paste is applied to a natural tooth and the attachment region 124 has an area of at least 50 square millimeters, after curing the paste can resist separation of the configurable arm 102 from the attachment region 124 when a force of 1 Newton is applied to the configurable arm 102 in any direction at a distance of 50 millimeters from the anchor region.

When the attachment region 124 is a ceramic surface (i.e., when the tooth 120 is not a natural tooth), the ceramic surface may not provide sufficient adhesion with the paste 112 for the paste 112 to be stably held. The system 100 can also include a bonding agent for application to the ceramic surface of the attachment region 124 prior to the application and curing of paste 112. The bonding agent can increase the stickiness of the ceramic surface of the attachment region 124. By increasing the stickiness of the ceramic surface prior to the application of the paste 112, sufficient adhesion force can be provided to prevent the paste 112 from inadvertently separating from the human jaw 128 during the procedure. In some embodiments, the bonding agent is light-curable. For example, the bonding agent may also be cured by example curing light device 300 shown in FIG. 3. An example light-curable bonding agent is Admira Bond, made by VOCO® GmbH.

In some embodiments, the configurable arm 102 has a weight of less than about 10 grams. The weight of the configurable arm 102 can affect the ability for the configurable arm 102 to maintain a shape or configuration as well as the adhesion force or attachment strength required of the paste 112 during the dental procedure.

In some embodiments, the system 100 can also include a registration computer configured for determining a registration of the human jaw 128 with a volumetric computed tomography (CT) image of the human jaw 128 stored in a computer-readable memory using exposed surfaces of the human jaw 128 outside of the selected attachment region 124, as described, for example, in U.S. patent application Ser. No. 16/037,517, titled "Jaw Surface Based Registration". In various embodiments, the registration computer can be operatively coupled to the pose tracking system 110. The system 110 may be distributed over a wide geographic area and the registration computer can communicate with the pose tracking system 110 via a network (not shown). The system 100 can include any appropriate communication component (not shown) to provide access to the network or enable communication between devices and systems.

In some embodiments, the registration computer can be integrated into the pose tracking system 110 to provide an integrated system configured for measuring changes to the pose of the at least one rigid target portion 106 and determining the registration of the human jaw with the volumetric CT image of the human jaw stored in a memory.

Figure 4:
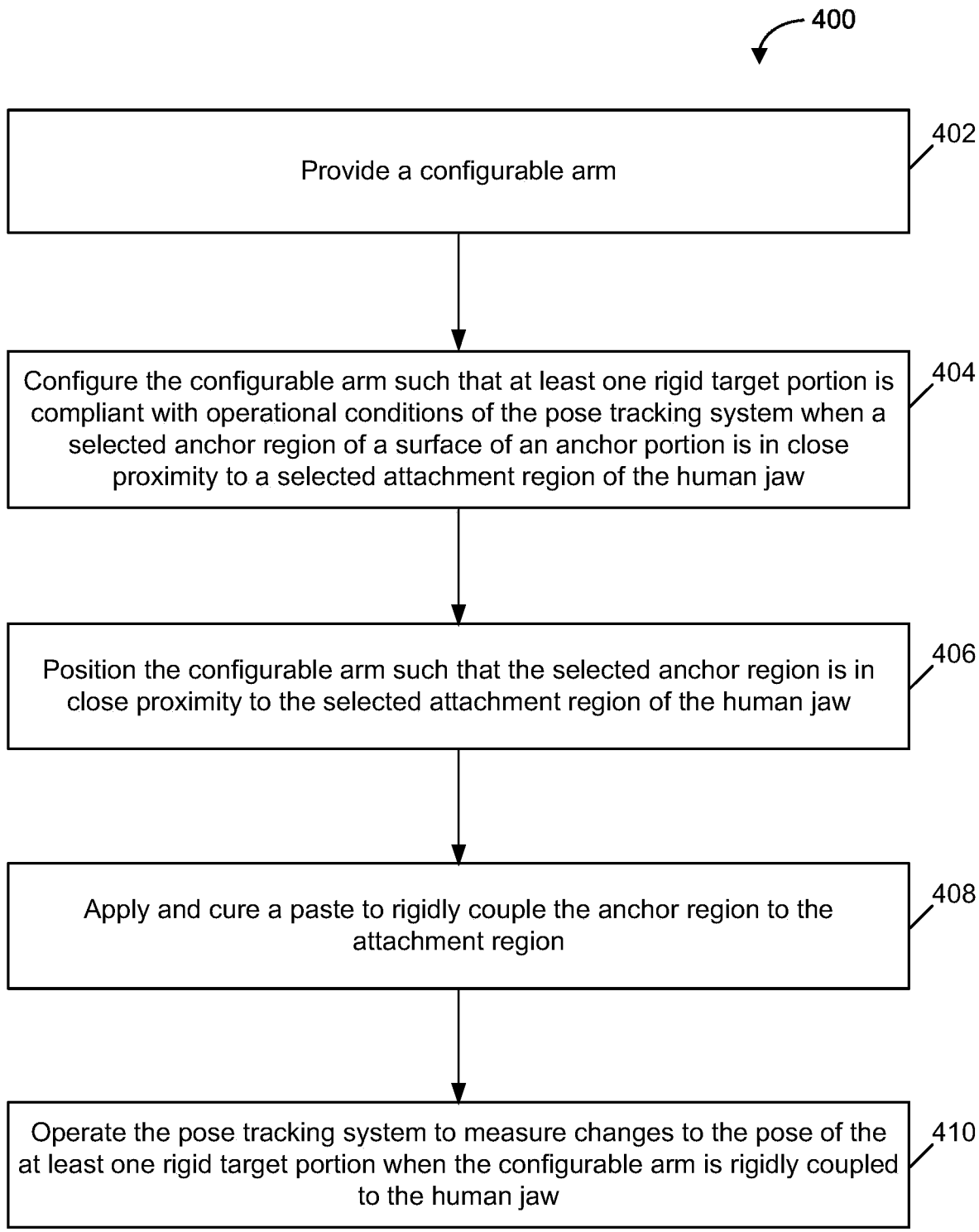
FIG. 4 is a flowchart of an example method for measuring changes in a pose of a human jaw within a coordinate system of a pose tracking system.

Referring now to FIG. 4, an example method 400 for measuring changes in a pose of a human jaw within a coordinate system of a pose tracking system is shown in a flowchart diagram. To assist with the description of the method 400, reference will be made simultaneously to FIG. 1.

At 402, a configurable arm, such as configurable arm 102 for example, is provided.

At 404, the configurable arm is configured such that the at least one rigid target portion 106 is compliant with the operational conditions of a pose tracking system, such as pose tracking system 110 for example, when a selected anchor region of a surface of the anchor portion 104 is in close proximity to a selected attachment region 124 of the human jaw 128. In some embodiments, the configurable arm 102 can include a metal wire; and configuring the configurable arm 102 at 404 involves bending the metal wire. The metal wire can be bent manually or, optionally with the aid of a tool, such as pliers.

At 406, the configurable arm is positioned such that the selected anchor region is in close proximity to the selected attachment region 124 of the human jaw 128.

At 408, a paste 112 is applied to coat the external surface attachment region 124 and cured to rigidly couple the anchor region to the attachment region 124.

At 410, the pose tracking system 110 is operated to measure changes to the pose of the at least one rigid target portion 106 when the configurable arm 102 is rigidly coupled to the human jaw 128. The changes to the pose of the at least one rigid target portion 106 is indicative of the changes in the pose of the human jaw 128.

In some embodiments, providing a configurable arm 102 at 402 involves selecting a metal wire biased to resume an initial shape after removal of a transient force of up to about 1 Newton at a distance of up to about 50 millimeters from the anchor region when the configurable arm 102 is rigidly coupled to the human jaw 128. The initial shape can define an initial spatial relationship between the anchor region and the at least one rigid target portion 106 prior to the transient force.

Furthermore, in some embodiments, providing a configurable arm 102 at 402 involves providing a configurable arm 102 with at least a portion of the anchor portion 104 shaped to resist rolling of the configurable arm 102 about its longitudinal axis within the paste 112 after the paste 112 is cured.

In some embodiments, the method 400 further involves applying a bonding agent to the selected attachment region 124 prior to applying the paste 112 at 408. A bonding agent can be applied to increase a stickiness of the selected attachment region 124, such as when the selected attachment region 124 is a ceramic surface region.

The method 400 can also include operating a computer and the pose tracking system 110 to determine a registration of the human jaw 128 with a volumetric computed tomography image of the human jaw 128 stored in a computer-readable memory using exposed surfaces of the human jaw 128 outside of the selected attachment region 124, as described, for example, in U.S. patent application No. Ser. No. 16/037,517, titled "Jaw Surface Based Registration".

In some embodiments, the at least one rigid target portion 106 is detachably coupled to the anchor portion 104. Accordingly, the anchor region is first positioned 406 in close proximity to the selected attachment region 124 of the human jaw, the paste 112 is applied and cured 408 to rigidly couple the anchor region to the attachment region 124, the at least one rigid target portion 106 is coupled or fastened to the anchor portion 104, and finally the configurable arm 102 is configured 404 such that the at least one rigid target portion 106 is compliant with the operational conditions of a pose tracking system 110.

Various embodiments have been described herein by way of example only. Various modification and variations may be made to these example embodiments without departing from the spirit and scope of the invention, which is limited only by the appended claims.

The invention claimed is:

1. A method for measuring changes in a pose of a human jaw within a coordinate system of a pose tracking system, the method comprising:
   (a) providing a configurable arm, the configurable arm comprising an anchor portion and at least one rigid target portion coupled to the anchor portion, a pose of the at least one rigid target portion being trackable by a tracking system when the at least one rigid target portion is compliant with operational conditions of the pose tracking system;

(b) configuring the configurable arm such that the at least one rigid target portion is compliant with the operational conditions of the pose tracking system when a selected anchor region of a surface of the anchor portion is in close proximity to a selected attachment region of the human jaw, the selected attachment region of the human jaw comprising a surface of at least one of the human jaw and a structure rigidly coupled to the human jaw;

(c) positioning the configurable arm such that the selected anchor region is in close proximity to the selected attachment region of the human jaw;

(d) applying and curing a paste to rigidly couple the anchor region to the attachment region, the paste comprising a light-curable polymer; and (e) operating the pose tracking system to measure changes to the pose of the at least one rigid target portion when the configurable arm is rigidly coupled to the human jaw, the changes to the pose of the at least one rigid target portion being indicative of the changes in the pose of the human jaw;

wherein the configurable arm comprises a metal wire, and configuring the configurable arm comprises bending the metal wire.

2. The method of claim 1, wherein the pose tracking system is an optical pose tracking system and the at least one rigid target portion comprises at least one of a retro-reflective region and a high contrast optical marking.

3. The method of claim 1, wherein providing a configurable arm further comprises selecting a metal wire biased to resume an initial shape after removal of a transient force of up to about 1 Newton at a distance of up to about 50 millimeters from the anchor region when the configurable arm is rigidly coupled to the human jaw, the initial shape defining an initial spatial relationship between the anchor region and the at least one rigid target portion prior to the transient force.

4. The method of claim 1, wherein providing a configurable arm further comprises providing at least a portion of the anchor portion shaped to resist rolling of the configurable arm about its longitudinal axis within the paste after the paste is cured.

5. The method of claim 4, wherein the at least a portion of the anchor portion shaped to resist rolling comprises at least one of a non-circular cross-section and a knurled surface.

6. The method of claim 1, wherein the paste further comprises a chemically-curable compound.

7. The method of claim 1, wherein the selected attachment region comprises an unetched surface of tooth enamel or dentin, and the paste is chemically adherable to the selected attachment region at an adhesion strength sufficient for attaching the configurable arm to the selected attachment region and resisting separation of the configurable arm from the selected attachment region when a force of 1 Newton is applied to the configurable arm in any direction at a distance of 50 millimeters from the anchor region.

8. The method of claim 1, wherein the paste has a viscosity in the range of about 10 Pascal second to about 250 Pascal second.

9. The method of claim 1, wherein the surface of at least one of the human jaw comprises a portion of a surface of a tooth of the human jaw.

10. The method of claim 1, wherein the structure rigidly coupled to the human jaw comprises at least one of an artificial crown and a dental implant screwed into the human jaw.

11. The method of claim 1, wherein the selected attachment region comprises a ceramic surface region, and the method further comprises applying a bonding agent to the ceramic surface region to increase a stickiness of the selected attachment region prior to applying the paste, the bonding agent being light-curable.

12. The method of claim 1 further comprising operating a computer and the pose tracking system to determine a registration of the human jaw with a volumetric computed tomography image of the human jaw stored in a computer-readable memory using exposed surfaces of the human jaw outside of the selected attachment region.

13. The method of claim 1, wherein the configurable arm has a weight of less than about 10 grams.

14. The method of claim 1, wherein the at least one rigid target portion being coupled to the anchor portion comprises the at least one rigid target portion being detachably coupled to the anchor portion.

15. The method of claim 1, wherein curing the paste further comprises applying an activation light to the paste coupling the anchor region to the attachment region to cure the light-curable polymer.

16. A system for measuring changes in a pose of a human jaw within a coordinate system of a pose tracking system, the system comprising:

(a) a configurable arm comprising an anchor portion and at least one rigid target portion, the anchor portion comprising an anchor region of a surface of the anchor portion, the configurable arm having a length sufficient for positioning the anchor region in close proximity to an attachment region of the human jaw while the at least one rigid target portion is compliant with operational conditions of the pose tracking system, the anchor region being rigidly securable by a light-curable paste to the attachment region of the human jaw, the attachment region of the human jaw comprising a surface of at least one of the human jaw and a structure rigidly coupled to the human jaw, the at least one rigid target portion being trackable by the pose tracking system; and (b) the pose tracking system configured for measuring changes to the pose of the at least one rigid target portion, the changes in the pose of the at least one rigid target portion being indicative of the changes in the pose of the human jaw;

wherein the configurable arm comprises a bendable metal wire.

17. The system of claim 16, wherein the pose tracking system is an optical pose tracking system and the at least one rigid target portion comprises at least one of a retro-reflective region and a high contrast reflective optical marking.

18. The system of claim 16, wherein the bendable metal wire comprises a wire biased to resume an initial shape after removal of a transient force of up to about 1 Newton at a distance of up to about 50 millimeters from the anchor region when the configurable arm is rigidly coupled to the human jaw, the initial shape defining an initial spatial relationship between the anchor region and the at least one rigid target portion prior to the transient force.

19. The system of claim 16, wherein at least a portion of the anchor portion of the configurable arm is shaped to resist rolling of the configurable arm about its longitudinal axis within the light-curable paste after the paste is cured.

20. The system of claim 19, wherein the at least a portion of the anchor portion shaped to resist rolling comprises at least one of a non-circular cross-section and a knurled surface.

21. The system of claim 16, further comprising the light-curable paste and the light-curable paste further comprising a chemically-curable compound.

22. The system of claim 21, wherein the attachment region comprises an unetched surface of tooth enamel or dentin, and the light-curable paste is chemically adherable to the attachment region at an adhesion strength sufficient for attaching the configurable arm to the attachment region and resisting separation of the configurable arm from the attachment region when a force of 1 Newton is applied to the configurable arm in any direction at a distance of 50 millimeters from the anchor region.

23. The system of claim 16, further comprising the light-curable paste, wherein the light-curable paste has a viscosity in the range of about 10 Pascal-second to about 250 Pascal-second.

24. The system of claim 16, wherein the surface of at least one of the human jaw comprises a portion of a surface of a tooth of the human jaw.

25. The system of claim 16, wherein the structure rigidly coupled to the human jaw comprises at least one of an artificial crown and a dental implant screwed into the human jaw.

26. The system of claim 16, the attachment region comprises a ceramic surface region, and the system further comprises a light-curable bonding agent for application to the ceramic surface region to increase a stickiness of the attachment region.

27. The system of claim 16, further comprising a computer configured for determining a registration of the human jaw with a volumetric computed tomography image of the human jaw stored in a computer-readable memory using exposed surfaces of the human jaw outside of the selected attachment region.

28. The system of claim 16, wherein the configurable arm has a weight of less than about 10 grams.

29. The system of claim 16, wherein the at least one rigid target portion is detachably couplable to the anchor portion.

30. The system of claim 16, further comprising a curing light device for emitting an activation light to cure the paste.

* * * * *